United States Patent [19]

Bae et al.

[11] Patent Number: 5,723,138
[45] Date of Patent: Mar. 3, 1998

[54] SKIN-ADHESIVE COSMETICS FOR REMOVING WRINKLES, CONTAINING VITAMINS AND ALOE EXTRACT

[76] Inventors: Jae-Hyun Bae; Ok-Yeon Kim, both of 47-3, Onchun-1 Dong, Tongrae-ku, Pusan, Rep. of Korea

[21] Appl. No.: 642,211

[22] Filed: May 6, 1996

[51] Int. Cl.$^6$ .................................................. A61K 7/48
[52] U.S. Cl. .......................... 424/401; 424/402; 424/443; 424/448
[58] Field of Search ................................. 424/401, 402, 424/443, 448

[56] References Cited

U.S. PATENT DOCUMENTS 5,306,504  4/1994  Lorenz ................................ 424/449
5,587,396  12/1996  Smith ................................ 514/557

*Primary Examiner*—Jyothsan Venkat
*Attorney, Agent, or Firm*—Michael N. Meller

[57] ABSTRACT

The present invention is to provide an adhesive type cosmetic product prepared by coating 5–50 parts by weight of the composition comprising 5–40% by weight of vitamin E, 5–50% by weight of vitamin A and 15–60% by weight of concentrated natural aloe extract, and 50–95 parts by weight of an adhesive in a mixture or in a laminate structure on a carrier film; and process for preparing thereof.

The adhesive type cosmetic product according to the present invention shows excellent effect for preventing, removing or alleviating wrinkles or furrows as compared to the conventional cosmetic compositions for removing wrinkles. In addition, the effect exhibited can be maintained for a long time and reappearance of furrows or wrinkles can be avoided, whereby providing very useful cosmetic product for removing wrinkles or furrows.

5 Claims, No Drawings

SKIN-ADHESIVE COSMETICS FOR REMOVING WRINKLES, CONTAINING VITAMINS AND ALOE EXTRACT

FIELD OF THE INVENTION

The present invention relates to skin-adhesive cosmetics for removing, preventing and/or alleviating wrinkles and/or furrows, which contains vitamin A, vitamin E and aloe extract, and a process for preparing thereof. More specifically, the present invention relates to skin-adhesive type or tape-type cosmetics in which vitamin A, vitamin E and concentrated aloe of natural origin are used as a mixture or a laminated structure, whereby maximizing the effects of the cosmetics including protection or removal of wrinkles (or deep furrows) and moisture-retaining effect, and a process for preparing thereof.

BACKGROUND OF THE INVENTION

The conventional cosmetic compositions for removing wrinkles can be divided into two groups consisting of a group originated from natural products extracted from animals or plants and a group prepared by the use of artificial synthetic products.

Referring to the prior art using natural extracts of animals or plants for prevention or treatment of wrinkles or shrinkage, a cosmetic composition containing human serum albumin as a main component with various additives (EP Laid-Open Patent EP-346189, EP-244859, EP-180960, Japanese Laid-Open Patent J6111831O); a composition comprising a coenzyme consisting of 5'-deoxyadenosyl cobalamine, flavin adenine dinucleotide (FAD), β-nicotinamide adenine dinucleotide (NAD), β-nicotinamide adenine dinucleotide phosphate (NADP) and pyrrole-quinaline quinone (PQQ), etc. having effects of preventing aging and alleviating wrinkles (EP Laid-Open Patent EP-256472, Japanese Laid-Open Patent J63152309, J63183535); a composition using byakuren extract (Japanese Laid-Open Patent J06065039); a composition comprising DNA extracted from fishes as a main component (Japanese Laid-Open Patent J06100426); a cosmetic composition comprising vitamin E as a main component with various vitamins as additives (EP Laid-Open Patent EP-158090, Japanese Laid-Open Patent J61040210, U.S. Pat. No. 5,093,360); a composition containing retinol (U.S. Pat. No. 5,093,360, EP Laid-Open Patent EP-391033); a composition comprising almond and sesame seed (Korean Laid-Open Patent 89-012631); and a composition comprising garlic as a main component (Korean Laid-Open Patent 84-003027) are disclosed.

Referring to the cosmetic compositions for removing wrinkles, prepared by using artificial synthetic material as main components, a cosmetic composition comprising N-acetyl-L-cysteine or its derivatives as a main component (U.S. Pat. No. 5,296,500, EP Laid-Open Patent EP-601088, International Laid-Open Patent WO9310755, WO9310756); a composition using specified synthetic amine derivatives (Japanese Laid-Open Patent J06271443, J06271449); a composition containing ascorbic acid, tyrosine and zinc salt (U.S. Pat. No. 4,938,969); a cosmetic composition comprising 3-phenylacetylamino-2,6-piperidinedione as a main component (U.S. Pat. No. 4,593,038, Japanese Laid-Open Patent J94076311); a composition containing benzoyl peroxide, phytelene and vitamin A (France Laid-Open Patent FR2687312); and a cosmetic composition for removing wrinkles, containing organic germanium compounds (U.S. Pat. No. 4,229,468, Japanese Laid-Open Patent J54073129) are disclosed.

Though the conventional Cosmetic compositions mentioned above exhibit their inherent characteristics, penetration of the active ingredients for removing wrinkles through the skin and the effect of moisture-retaining cannot be fully expected because they are used as a cosmetic product for applying on the skin as a cream, ointment or milk lotion type, so that the solvent contained in the product may evaporate as time goes by after the application to cause hardening of the product. In addition, the conventional compositions have some problems in that even though an instant effect of alleviating or removing wrinkles once occurred, the wrinkles appear after a certain time, and they sometimes have skin irritating problems.

SUMMARY OF THE INVENTION

The present invention was invented in order to solve the problems of the prior art mentioned above, and the object of the invention is to provide a cosmetic product for removing, preventing, or alleviating furrows, wrinkles or shrinkage of skin without irritation, by virtue of effective and continuous skin penetration of the cosmetic composition, and to provide a process for preparation thereof.

As a result of intensive studies, the present inventors found that a tape-type or skin adhesive type cosmetic product prepared by coating active ingredients comprising vitamin A, vitamin E and aloe extract together with an appropriate adhesive on a non-toxic carrier can achieve the object mentioned above, and completed the invention.

DETAILED DESCRIPTION OF THE INVENTION

The cosmetic composition excluding the tape (carrier) and adhesive of the cosmetic product of the present invention (hereinafter, referred to as "cosmetic composition of the present invention") comprises 5–40 parts by weight, preferably 10–30 parts by weight of natural tocopherol (vitamin E), 5–50 parts by weight, preferably 15–35 parts by weight of vitamin A), 0.1–5 parts by weight of vitamin stabilizer and 0.01–0.1 part by weight of vasodilatory agent. In addition, 15–60 parts by weight of concentrated natural aloe extract is contained in the cosmetic composition of the present invention in order to promote the physiological activity of the skin and to assist the support and continuous penetration of vitamin components on the skin. Besides, an appropriate amount of surface active agent may be used, if required, in order to make a completely intimate mixture of water-soluble aloe extract and oil-soluble vitamins. Further, an appropriate amount of antioxidant and/or preservatives may be used in order to prevent denaturation of active ingredients, and pigments may be added, if required.

The vitamin A or vitamin E component used in the present invention may have any conventional type or appearance of those used in the field of cosmetics or pharmaceuticals. For example, vitamin A maybe used as retinol (Vit $A_1$), retinal or vitamin A palmitate, while vitamin E may be used as α-tocopherol or tocopheryl acetate.

The vitamin stabilizers, surface active agents, antioxidants, vasodilatory agents, preservatives or pigments may be selected from those conventionally used in the field of cosmetic industry. Referring to the non-limiting examples, the vitamin stabilizer includes polyethylene glycol, polypropylene glycol or mixture thereof, the surface active agent includes hydrophilic surface active agent such as triethanolamine, polysorbate 60 (Tween 60), and/or lipophilic surface active agent such as stearic acid, Cerasynt SD, Lanett-0, sorbitan sesquioleate (Arlacel 83) and Carboset, and antioxidant include methyl paraben and/or propyl paraben.

The cosmetic composition of the present invention can be prepared by a conventional process in the art in a form of emulsion (lotion), cream, ointment or gel.

In order to maximize the effect of preventing, removing and/or alleviating the furrows and wrinkles of skin, the present invention is characterized in that the cosmetic composition prepared as mentioned above is coated on a non-toxic carrier in a mixture of non-toxic adhesive or in a laminate type to manufacture a tape-type or adhesive type cosmetic product.

As an adhesive, any conventional adhesives used in adhesive type preparations may be used if it is non-toxic to human body. For example, Acrezol AR-430F (transparent), polybutene, polyvinyl alcohol (PVA), latex emulsion or gelatin may be used. An adhesive which is readily adhered by slight pressure and readily removed after a certain time may be used. The amount of the adhesives is 50–95%, preferably 80–90% of the total weight of adhesives and the cosmetic composition of the present invention comprising the active ingredients. If the amount is less than 50% by weight, adhesive strength may be lowered owing to the inhomogeneity between the adhesive and the cosmetic composition and side-effects may occur owing to the excess use of vitamins, while the expected object cannot be achieved if the amount is more than 95% by weight. In order to assist the performance of the adhesives, a curing agent such as Acrezol AR-430F and/or a sticking assistant agent such as HI-KOREZ A-1100, A-1100S or T-1080 may also be used.

The type of carriers used is not limited. Transparent, semi-transparent or opaque polymeric film, soft fabrics or paper may be used. A transparent polymeric film having a thickness of 20–100 µm may be preferably used.

According to an embodiment of the present invention, a tape type or adhesive type cosmetic product is prepared by mixing the above cosmetic composition with an adhesive; coating the mixture on a carrier; drying thereof; and covering a releasing paper thereon to protect the ingredients of the composition till the time of use. The thickness of the coated composition is 5–50 µm, preferably 20–30 µm.

According to another embodiment of the present invention, a cosmetic product is prepared by forming an adhesive layer of 1–5 µm thickness on a carrier film; drying thereof; coating the cosmetic composition of the present invention in a thickness of 5–50 µm, preferably 20–30 µm; coating an adhesive in a thickness of 1–5 µm thereon; drying thereof; and protecting thereof with a releasing paper. In this case, the process is somewhat lengthened, but the disadvantages of reduction of viscosity or retardation of skin penetration of the composition owing to the mixing of the cosmetic composition with the adhesive, may be overcome. In addition, the process is advantageous in that additional emulsifier or a surface active agent for mixing the cosmetic composition with adhesive is not required.

According to still another embodiment of the present invention, an adhesive type cosmetic product is prepared by forming an adhesive layer of 1–5 µm thickness on a carrier; coating concentrated aloe extract in a thickness of 10–20 µm; coating a mixture of the remaining ingredients other than aloe with adhesive thereon in a thickness of 5–50 µm, preferably 20–30 µm; drying thereof; and covering a releasing paper thereon. In this case, the process is somewhat lengthened, but advantageous in that a vigorous stirring process at high temperature for direct mixing of water-soluble aloe extract and oil-soluble vitamins in the said cosmetic composition can be avoided.

During the process for the preparation of the adhesive cosmetic product according to the present invention as described above, the thickness of the composition and/or adhesives can be adjusted by altering the concentration of the solution to be coated and the revolution rate of the roll. The thickness of the composition and/or adhesive layer can be measured by using an α-step depth profilor.

Alternatively, a similar effect as in the case of the adhesive cosmetic product of the present invention can be obtained if a lotion is prepared by a conventional method by adding 20–40% by weight of unsaturated fatty acid and 30–50% by weight of glycerine to the said cosmetic composition, and the lotion is applied on skin, and then a polymeric film on which only adhesive has been coated is adhered onto the skin. This method includes cumbersome process for use, however, the mixing step of the cosmetic composition with the adhesives can be omitted, and rapid transmission of the active ingredients to skin can be expected.

A preferable use of the tape type adhesive cosmetic product according to the present invention includes adhering the product on a region in which the removal of wrinkles is desired, and then removing the product at the time of washing the face in the morning. The cosmetic product according to the present invention can be readily removable from skin without any pain or irritation.

The method of using the adhesive type cosmetic product, and the method of applying the cosmetic composition followed by adhering the adhesive film exhibit prominent effect of removing the furrows or wrinkles than that of the conventional cosmetic products for the same object. In addition, the effect exhibited can be maintained for a long time and reappearance of furrows or wrinkles can be avoided by the use of the product of the present invention. The effects mentioned above have been proved by experimental examples described hereinbelow.

The excellent effect of the adhesive type cosmetic product of the present invention as compared to those cosmetics of applying type is due to the effect of the adhesive tape itself which induces continuous penetration of the active ingredients and protects the ingredients and physically stretches the skin, as well as the effect of the cosmetic composition per se.

DETAILED DESCRIPTION OF THE PREFERRED EMBODIMENT

Hereinafter, the preparations of cosmetic compositions and adhesive cosmetic products according to the present invention, and experiments for proving the effects are described in detail by referring to the Examples and Experimental Examples. However, it is apparent that the present invention is not limited to these Examples.

EXAMPLES 1–5

A process for preparing the cosmetic composition is described. If required, the composition may be used only as aqueous phase or oil phase, or the necessary ingredients from the aqueous phase or oil phase may be selectively used.

At first, in order to prepare the aqueous phase, aloe extract, triethanolamine, Tween 60 and methyl paraben were mixed at 70° C. by stirring at a rate of 3000 rpm for 5 minutes to obtain an intimate mixture.

In a separate vessel, in order to prepare the oil phase, vitamin A palmitate, vitamin E, stearic acid, Cerasynt SD, Lanett-0, Arlacel 83 and propyl paraben were mixed at 50° C. by stirring at a rate of 3000 rpm for 5 minutes to obtain an intimate mixture.

The obtained oil phase is added to the aqueous phase, and the resultant mixture is stirred at 5500 rpm for about 5 to 10 minutes as maintaining the temperature at 70° C. After cooling the mixture to 50° C., Carboset is added, and then the mixture is cooled to room temperature. If desired, purified water may be added. In order to obtain a cosmetic composition of lotion type, unsaturated fatty acid or base wax and/or glycerine is(are) added thereto to adjust the viscosity.

The composition of each cosmetic composition is shown in Table 1 below.

TABLE 1

| Component | Ex.1 | Ex.2 | Ex.3 | Ex.4 | Ex.5 |
|---|---|---|---|---|---|
| Vitamin A palmitate | 10 | 30 | 20 | 20 | 15 |
| Vitamin E | 10 | 30 | 25 | 25 | 15 |
| Conc. aloe extract | 40 | 20 | 30 | (35) | 25 |
| polyethyleneglycol | 0.5 | 1.5 | 0.8 | 0.5 | 0.5 |
| Vasodilatory agent | 0.05 | 0.1 | 0.05 | 0.05 | 0.05 |
| Triethanolamine | 1 | 1 | 10 | — | 2 |
| Tween 60 | 0.3 | 0.3 | 0.6 | — | 0.6 |
| Stearic acid | 2 | 2 | 2 | — | 4 |
| Cerasynt SD | 1 | 1 | 2 | — | 2 |
| Lanett-O | 3 | 3 | 6 | — | 6 |
| Arlacel 83 | 0.3 | 0.3 | 0.6 | — | 0.6 |
| Methyl paraben | 0.25 | 0.25 | 0.5 | 0.5 | 0.5 |
| Propyl paraben | 0.1 | 0.1 | 0.2 | 0.2 | 0.2 |
| Carboset | 30 | 10 | 4 | — | 8 |
| Unsaturated fatty acid | — | — | — | — | 10 |
| Glycerine | — | — | — | — | 5 |
| Base wax | — | — | — | — | 5 |
| Purified water | To 100 | To 100 | To 100 | — | To 100 |

EXAMPLES 6–10

Tape-type or adhesive type cosmetic products were prepared by using adhesives and the cosmetic composition obtained in Examples 1–5.

In Examples 6 and 7, the mixed composition having a composition listed in Table 2 below was coated in 30 μm thickness on a transparent polymeric film having 50 μm of thickness, and dried in an oven at 120° C. for 3 minutes, and then a releasing paper was covered thereon.

In Example 8, an adhesive was firstly coated in 5 μm thickness, and the composition of Example 3 was coated thereon in a thickness of 25 μm, and then an adhesive was coated thereon again. After each step of coating the adhesive, a drying step in an oven at 120° C. for 3 minutes should be performed.

In Example 9, an adhesive was firstly coated in 5 μm thickness, and aloe component of Example 4 was coated thereon, and then a mixture of the adhesive with remaining components of Example 4 was coated thereon in 25 μm thickness, and dried in an oven at 120° C. for 3 minutes.

In Example 10, the composition of Example 5 was applied on skin and a polymeric film coated with the adhesive of Example 10 was adhered thereon.

TABLE 2

| Components | Ex.6 | Ex.7 | Ex.8 | Ex.9 | Ex.10 |
|---|---|---|---|---|---|
| Acrezol AR-430F (transparent) | 80 | 90 | 80 | 85 | 85 |
| Acrezol AR-430F (Curing agent) | 0.8 | 1 | 0.5 | 0.8 | 0.8 |
| HI-KOREZ A-1100S | — | 2 | — | — | — |
| Lead oxide | — | Proper amount | — | — | — |
| Composition of Ex.1 | 10 | — | — | — | — |
| Composition of Ex.2 | — | 5 | — | — | — |
| Composition of Ex.3 | — | — | (15) | — | — |
| Composition of Ex.4 | — | — | — | (10) | — |
| Composition of Ex.5 | — | — | — | — | (10) |
| Ethyl acetate | To 100 | To 100 | To 100 | To 100 | To 100 |

EXPERIMENTAL EXAMPLE 1

Removal of Wrinkles

The experiment was performed by twenty(20) women more than 30 years old.

At night, after washing the face, moisture was removed and commercially available night cream was applied to the face. After 1–3 minutes, the cosmetic product prepared by Example 6 was adhered on the left eye rim, and then it was removed next morning. After performing the procedure everyday for 1 month, the effect of the cosmetic product of the present invention was estimated as compared to that of right eye rim (control).

In addition, after the experimental period, the use of the cosmetic product of the present invention was quit, and the disappearance of the effect was observed. The results are shown in Table 3 below.

TABLE 3

| Effects | No. of persons (%) |
|---|---|
| Prominent reduction or removal of wrinkles | 4 (20%) |
| Considerable reduction of depth of wrinkles | 12 (60%) |
| Slight alleviating the condition of wrinkles | 3 (15%) |
| Not sensitive | 1 (5%) |

Further, among the nineteen (19) persons who experienced the effect of alleviating and/or removing of wrinkles after 1 month use, seventeen (17) persons (89%) felt the effect of the present cosmetic product on the left eye rim as compared to the right eye rim after seven days from quitting the use of the product, whereby the excellent maintenance of the effect of removing wrinkles of the present cosmetic product has been confirmed.

EXPERIMENTAL EXAMPLE 2

Removal of Deep Furrows

For twenty (20) people who have deep furrows on his(her) forehead, the effect of the present cosmetic product for the removal of deep furrows has been examined. The experimental procedure was similar to that of Experimental Example 1.

Results are shown in Table 4 below.

TABLE 4

| Effects | No. of persons (%) |
| --- | --- |
| Prominent reduction or removal of furrows | 3 (15%) |
| Considerable reduction of depth of furrows | 8 (40%) |
| Slight alleviating the condition of furrows | 9 (45%) |
| Not sensitive | 0 (0%) |

EXPERIMENTAL EXAMPLE 2

Skin irritation

For fifty (50) adults (men and women) who are twenty (20) or more years old, skin irritation of the present cosmetic product was examined. On the armpit side of upper arm, the tape type cosmetic product prepared in Example 7 was adhered, and after 12 hours, the occurrence of irritation, red spot, itching or allergy has been examined.

The results are shown in Table 5.

TABLE 5

| Skin irritation | No. of persons (%) |
| --- | --- |
| No alteration occurred | 45 (90%) |
| After removing the product, itching occurred, but instantly disappeared | 2 (4%) |
| The adhered region appeared to be red, but became normal after 1-2 hours | 3 (6%) |
| Considerable irritation occurred | 0 (0%) |

As exhibited in these Experimental Examples, the adhesive type cosmetic products prepared according to the present invention have excellent effect of removing or alleviating wrinkles or furrows (95%), and excellent maintenance of said effect, without substantial irritation on the skin where they had been adhered.

What is claimed is:

1. An adhesive cosmetic product which comprises a coating of a cosmetic composition and a nontoxic adhesive in a mixture or in a laminate structure on a non-toxic carrier film, and which may be directly adhered to the regions of the skin and removed easily from the skin wherein the cosmetic product comprises a coating of 5–50 parts by weight of the composition comprising 5–40% by weight of vitamin E, 5–50% by weight of vitamin A and 15–60% by weight of concentrated natural aloe extract, and 50–95 parts by weight of an adhesive in a mixture or in a laminate structure on a carrier film, wherein the cosmetic composition is in a thickness of from 5–50 μm and the adhesive is in a thickness of from 1–5 μm.

2. An adhesive cosmetic product according to claim 1 wherein the composition comprises 10–30% by weight of vitamin E, 10–30% by weight of vitamin A and 30–60% by weight of concentrated natural aloe extract.

3. A process for preparing an adhesive cosmetic product comprising coating a cosmetic composition and a non-toxic adhesive in a mixture or in a laminate structure onto a non-toxic carrier to form a tape-type, adhesive type, or patch type cosmetic product, wherein 5–50 parts by weight of the composition comprising 5–40% by weight of vitamin E, 5–50% by weight of vitamin A and 15–60% by weight of concentrated natural aloe extract, and 50–95 parts by weight of an adhesive are coated in a mixture or in a laminate structure on a carrier film, further comprising the steps of forming an adhesive layer of 1–5 μm thickness on a carrier film; drying thereof; coating the cosmetic composition of the present invention in a thickness of 5–50 μm; coating an adhesive in a thickness of 1–5 μm thereon; drying thereof; and protecting thereof with a releasing paper.

4. A process according to claim 3, which comprises the steps of forming an adhesive layer of 1–5 μm thickness on a carrier; coating a concentrated aloe extract in a thickness of 10–20 μm; coating a mixture of the remaining ingredients other than aloe with adhesive thereon in a thickness of 5–50 μm; drying thereof; and covering a releasing paper thereon.

5. An adhesive cosmetic product according to claim 1, wherein the carrier is a transparent, semi-transparent or opaque polymeric film, or a soft fabric or paper.

* * * * *